United States Patent [19]

Feakins

[11] 4,265,876
[45] May 5, 1981

[54] ANIMAL EAR-TAGS, THEIR MANUFACTURE AND THEIR USE

[75] Inventor: Patrick G. Feakins, Ashford, England

[73] Assignee: Shell Internationale Research Maatschappij B.V., Netherlands

[21] Appl. No.: 14,047

[22] Filed: Feb. 22, 1979

[30] Foreign Application Priority Data

Mar. 7, 1978 [GB] United Kingdom ............... 9001/78

[51] Int. Cl.³ .................. A61F 13/00; A01N 37/34; A01N 37/00; G09F 3/00
[52] U.S. Cl. ................................. 424/28; 40/300; 40/301; 424/78; 424/304; 424/305
[58] Field of Search ............... 424/28, 78, 304, 305; 40/300, 301

[56] References Cited

U.S. PATENT DOCUMENTS

| | | | |
|---|---|---|---|
| 3,852,416 | 12/1974 | Grubb et al. | 424/28 |
| 3,942,480 | 3/1976 | Hair et al. | 119/156 |
| 3,949,708 | 4/1976 | Meeks | 40/301 |

FOREIGN PATENT DOCUMENTS

1337882 11/1973 United Kingdom .

OTHER PUBLICATIONS

Chem. Abst-86, (12565b), (1977).
Chem. Abst-87, 162727R, 178973d, (1977).
Chem. Abst. 88-33129U, (1978).

*Primary Examiner*—Stanley J. Friedman

*Attorney, Agent, or Firm*—Pravel, Gambrell, Hewitt, Kirk, Kimball & Dodge

[57] ABSTRACT

The invention relates to animal ear tags.

Ear tags for attachment to ears of animals such as cattle in accordance with the invention are made at least in part from a material comprising a solid organic polymeric macromolecular substance having a molecular weight above 1000 and a pesticidally-active compound having the general formula:

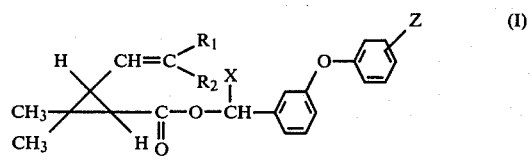

wherein $R_1$ and $R_2$ are independently selected from fluorine, chlorine and bromine; X is hydrogen, cyano or ethynyl; and Z is hydrogen, chlorine, fluorine or bromine. The invention also provides a method for making the tags by mixing the macromolecular substance and the compound of formula I and forming the tag by injection moulding, and further provides a method of controlling fly and tick populations in the vicinity of an animal by affixing to an ear of the animal a tag in accordance with the invention.

The ear tags are surprisingly effective in the control of insects and ticks on animals, such as cattle.

9 Claims, No Drawings

ANIMAL EAR-TAGS, THEIR MANUFACTURE AND THEIR USE

This invention relates to animal ear-tags, to a method of making them and to methods of using them in controlling fly and tick populations.

Ear-tags which are clipped to the ears of animals for identification purposes are well known. Such tags can be made of a plastics material or of a suitable metal and can take the form of a single element or band, one end of which is capable of piercing an animal ear and making a firm connection with the other end of the element or band; alternatively they can take the form of a two-component tag comprising a male component having a pointed pin which is adapted to be forced through an animal ear and a female component which can be urged over the pointed end of the pin to retain the male component in position on the ear. The means of identification, i.e., the tag itself, can be attached to or integrally formed with the single element or band or either or both components of the two-component tag, U.K. Patent No. 1,337,882 describes a two-component tag and also illustrates a pair of modified pliers for attaching such tags to animal ears.

The Applicant has found that, by forming ear-tags from a plastics material containing a certain pesticide, remarkable control of pests, especially cattle pests, can be achieved with animals wearing such ear-tags.

Accordingly, the present invention provides an ear-tag for attachment to an ear of an animal wherein at least part of the tag is made from a material comprising a solid organic polymeric macromolecular substance having a molecular weight above 1000 and a pesticidally-active compound having the general formula:

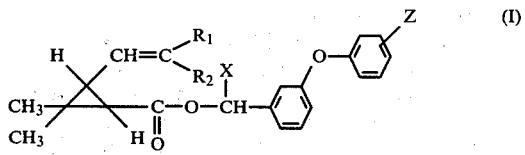

wherein $R_1$ and $R_2$ are independently selected from fluorine, chlorine and bromine; X is hydrogen, cyano or ethynyl; and Z is hydrogen, chlorine, fluorine or bromine. In the general formula I, X is preferably hydrogen or cyano and Z is preferably hydrogen.

The whole tag may be formed of the said material. Alternatively, only part of the tag, for example a single component of a two-component tag, may be made of the said material. Conveniently the tag is formed entirely of the said material.

It will be appreciated that the pesticidally-active compounds of general formula I have a number of asymmetric carbon atoms present in their structures and thus give rise to a corresponding number of isomers. Accordingly, the invention also includes an ear-tag made at least in part from a material comprising a polymeric macromolecular substance and a compound of the general formula I in the form of a single isomer or of a mixture of 2 or more such isomers.

Examples of preferred pesticidally-active compounds for use in the ear-tag according to the invention are:

(i) alpha-cyano-3-phenoxybenzyl 2,2-dimethyl-3-(2,2-dichlorovinyl)cyclopropane carboxylate;

(ii) alpha-cyano-3-phenoxybenzyl 2,2-dimethyl-3-(2,2-dibromovinyl)cyclopropane carboxylate;

(iii) alpha-cyano-3-phenoxybenzyl 2,2-dimethyl-3-(2,2-difluorovinyl)cyclopropane carboxylate;

(iv) 3-phenoxybenzyl 2,2-dimethyl-3-(2,2-dichlorovinyl)cyclopropane carboxylate;

(v) 3-phenoxybenzyl 2,2-dimethyl-3-(2,2-dibromovinyl)cyclopropane carboxylate;

(vi) 3-phenoxybenzyl 2,2-dimethyl-3-(2,2-difluorovinyl)cyclopropane carboxylate;

(vii) 3-phenoxybenzyl (1R, 1S, cis)-2,2-dimethyl-3-(2,2-dichlorovinyl)cyclopropane carboxylate;

(viii) 3-phenoxybenzyl (1R, cis)-2,2-dimethyl-3-(2,2-dichlorovinyl)cyclopropane carboxylate;

(ix) (R, S)-alpha-cyano-3-phenoxybenzyl (1R, cis)-2,2-dimethyl-3-(2,2-dichlorovinyl)cyclopropane carboxylate;

(x) (R, S)-alpha-cyano-3-phenoxybenzyl (1R, cis)-2,2-dimethyl-3-(2,2-dibromovinyl)cyclopropane carboxylate;

(xi) (R, S)-alpha-cyano-3-phenoxybenzyl (1R, cis)-2,2-dimethyl-3-(2,2-difluorovinyl)cyclopropane carboxylate;

(xii) (S)-alpha-cyano-3-phenoxybenzyl (1R, cis)-2,2-dimethyl-3-(2,2-dichlorovinyl)cyclopropane carboxylate;

(xiii) (S)-alpha-cyano-3-phenoxybenzyl (1R, cis)-2,2-dimethyl-3-(2,2-dibromovinyl)cyclopropane carboxylate; and (xiv) (S)-alpha-cyano-3-phenoxybenzyl (1R, cis)-2,2-dimethyl-3-(2,2-difluorovinyl)cyclopropane carboxylate.

The solid polymeric organic macromolecular substance present in the ear-tag according to the invention has a molecular weight of above 1000. The polymeric macromolecular substance may be thermosetting or thermoplastic, although the latter is more readily employed in the manufacture of an ear-tag of the invention. Examples of suitable macromolecular substances are polyolefins (for example polyethylene, polypropylene and copolymers of ethylene and propylene); polyacrylates (for example polymers and copolymers of methyl acrylate, ethyl acrylate, methyl methacrylate and ethyl methacrylate); polymers of vinyl compounds (for example polystyrene and polymerized divinylbenzene); polyvinyl halides (for example polyvinyl chloride); polyvinyl acetals (for example polyvinyl butyral); polyvinylidene compounds (for example polyvinylidene chloride); synthetic and natural elastomers (for example rubber obtained from *hevea brasiliensis*, cis-1,4-polyisoprene, polybutadiene and SBR rubber); urea-formaldehyde and melamine-formaldehyde resins; epoxy resins (for example polymers of polyglycidyl ethers of polyhydric phenols); cellulose plastics (for example cellulose acetate, cellulose butyrate and cellulose nitrate); and polyurethanes. Choice of the macromolecular substance will depend both on the particular pesticide with which it is to be formulated and the conditions under which the final formulation will be employed. The macromolecular substance, to be most effective, must be insoluble in water and present a hydrophobic surface, thus resisting the absorption of moisture on its surface.

Preferably, the macromolecular substance is a polymer or a copolymer of a vinyl compound, for example polyvinyl halides (for instance polyvinyl chloride and polyvinyl fluoride); polyacrylate and polymethacrylate esters (for instance polymethyl acrylate and polymethyl methacrylate); and polymers of vinyl benzenes (for instance, polystyrene and polymer polymerized vinyl toluene). Because it combines the most desirable physical properties with the most compatibility for the pesticide the most preferred macromolecular substances are polymers or copolymers of vinyl chloride.

It is generally necessary to include a plasticizer in the material in order to enable satisfactory ear-tags to be formed from it. Examples of plasticizers are phthalates (for example dioctyl phthalate, diphenyl phthalate, dicyclohexyl phthalate, dimethyl phthalate and dihexyl phthalate); sebacates (for example dipentyl sebacate, n-butyl benzyl sebacate and dibenzyl sebacate); and adipates (for example dioctyl adipate, dicapryl adipate, di-isobutyl adipate and dinonyl adipate). Other compatible plasticizers are, for example, hydrogenated polyphenols; alkylated aromatic hydrocarbons; and polyester plasticizers, for example polyesters of polyols, such as hexanediol, and polycarboxylic acids, such as sebacic or adipic acid, having molecular weights of about 2000.

Other materials (for example, dyes, pigments, lubricants, fillers, anti-oxidants and ultraviolet stabilizers) may be included in the material. For example, it has been found that the stability of both the macromolecular substance and the pesticide is extended if a stabilizing amount, preferably 0.1% w to 10% w, of a phenol is included in the material; for example, phenol, p-cresol, m-cresol, hydroquinone, resorcinol and pyrogallol are effective as stabilizers. The phenols are preferably unsubstituted and alkyl-substituted mono- and di-hydroxybenzenes wherein the alkyl groups have not more than eight carbon atoms. Particularly preferred phenols are phenolic anti-oxidants, for example mononuclear phenols having a phenolic hydroxyl group which is hindered by one or more ortho-alkyl groups (for example 2,6-dialkyl phenols, for instance 2,6-di-tert.butyl-4-methyl phenol; 2,4,6-tri-tert.butyl phenol; 2,6-di-tert.butyl phenol; 2-methyl-6-tert.butyl phenol; 2,4-dimethyl-6-tert.butyl phenol and 2,6-di-isopropyl-4-methyl phenol). Also preferred are, for example, bisphenolic and biphenolic stabilizers (for example bis-(3,5-di-tert.butyl-4-hydroxyphenyl)methane; bis-(2-hydroxy-3-tert.butyl-5-methylphenyl)methane and 3,3'-5,5'-tetra-tert.butyl-4,4'-dihydroxy biphenyl); naphthols (for example beta-naphthol) and benzyl alcohols (for instance 3,5-di-tert.-butyl-4-hydroxybenzyl alcohol; 3,5-di-isopropyl-4-hydroxybenzyl alcohol and 3-methyl-5-tert.butyl-4-hydroxybenzyl alcohol).

The ear-tag may be manufactured by any convenient means, for example by injection moulding techniques. The concentration of the pesticide in the ear-tag may vary between 0.5 and 25% by weight and preferably lies in the range of from 1 to 20% by weight. The most preferred concentration range is from 5 to 15% by weight, and the concentration is advantageously about 10% by weight of the ear-tag. Concentrations falling in these ranges have produced good results in terms of fly and tick control.

Whilst it has been established that the pesticides of formula I (known as synthetic pyrethroids) have a high level of insecticidal activity, it was surprising to find that an animal bearing an ear-tag according to the invention remains substantially free from flies and other insects especially ticks for a period of up to 3 months or more. It is assumed that the effectiveness of the ear-tag must be due, at least in part, to the migration of the pesticide from the ear-tag to its surface and from there to the coat of the animal, the latter migration being presumably due to the natural movement of the animal and its ears. A considerable advantage of the invention results in the fact that the use of ear-tags for identification purposes is a necessary and well-established practice and that the ear-tag according to the invention may be identical in shape and appearance with existing ear-tags but has the additional valuable property of maintaining an animal bearing such a tag in a substantially fly-free condition.

The invention also includes within its scope a method of controlling fly and tick populations on or in the vicinity of an animal which comprises affixing to the ear of the animal an ear-tag according to the present invention. The two-component tag referred to hereabove and in the Example may be affixed to the ear of an animal by means of an applicator in the form of a pair of pliers with each component attached to a jaw of the applicator; on closing the applicator the pin on one component pierces the animal ear and then is forced through a hole in the other component to complete installation of the tag on the animal ear, as described, for example, in U.K. Patent No. 1,337,882.

If desired, other pesticides may be incorporated into the tag in order to augment or extend the spectrum of activity of the pesticide having general formula I.

The invention is further illustrated by the following Examples:

EXAMPLES 1 and 2

During the summer period when fly infestations are a problem, thermoplastic two-component ear-tags having incorporated therein the following two pesticidally-active compounds at a concentration of 10% by weight were attached to the left ears of 35 young bulls:

Example 1 Compound: alpha-cyano-3-phenoxybenzyl 2,2-dimethyl-3-(2,2-dichlorovinyl)cyclopropane carboxylate.

Example 2 Compound: 3-phenoxybenzyl 2,2-dimethyl-3-(2,2-dichlorovinyl)cyclopropane carboxylate.

The tagged bulls were placed in a field and a fly count was taken at intervals over a period of 31 days for each bull, 35 untagged bulls were kept in a separate field and similar fly counts were also taken for the same period so that the effectiveness of the ear tags could be properly assessed.

The results of the fly counts represented as mean fly-counts per animal over a 31-day period are given in the following Table, the principal fly species infesting the animals being:

Musca domestica;
Musca autumnalis;
Haematobia irritans; and
Stomoxys calcitrans.

TABLE

| Day of fly-count over 31-day period | Mean fly-count per animal | | |
|---|---|---|---|
| | Example 1 | Example 2 | control |
| day 2 | 1.9 | 2.2 | 15.6 |
| day 10 | 0 | 0 | 3.5 |
| day 13 | 0 | 0 | 3.9 |
| day 15 | 0 | 0 | 1.4 |
| day 16 | 0 | 0.2 | 4.6 |
| day 17 | 1.2 | 1.4 | 11.4 |
| day 21 | 0.5 | 0.5 | 7.1 |
| day 22 | 0.2 | 0.3 | 4.8 |
| day 23 | 0.2 | 0.2 | 32.5 |
| day 24 | 0 | 0.2 | 28.0 |
| day 27 | 1.2 | 3.0 | 68.1 |
| day 28 | 0 | 0 | 42.3 |

TABLE-continued

| Day of fly-count over 31-day period | Mean fly-count per animal | | |
| --- | --- | --- | --- |
| | Example 1 | Example 2 | control |
| day 29 | 1.5 | 2.1 | 32.3 |
| day 30 | 0.3 | 0.5 | 33.7 |
| day 31 | 0 | 0.2 | 36.8 |

It will be seen from these results that the ear-tags provide consistently-good protection against flies, even on days when the control fly population was high, e.g., on days 27, 28 and 31.

It was concluded that such effective results could only be achieved if the pesticidal component in the ear-tag migrated to the surface of the tag and thence over the coat of the animal, this migration being brought about by the natural movement of the animal and its ears.

In the Examples the ear-tags were manufactured from polyvinyl chloride (PVC) including a plasticizer and one of the Example 1 or 2 compounds in a concentration of 10% by weight and were formed by injection moulding. The tags took the form of a two-component tag having a male component in the form of a pointed pin which can be forced through an animal ear and a female component which can be urged over the pointed end of the pin to retain the male component in position on the ear, as described in U.K. Patent No. 1,337,882.

The claims defining the invention are as follows:

1. An animal ear tag for attachment to an ear of an animal, characterized in that at least part of the tag is made from a material comprising a solid organic polymeric macromolecular substance having a molecular weight above 1000 and a pesticidally-active compound having the general formula:

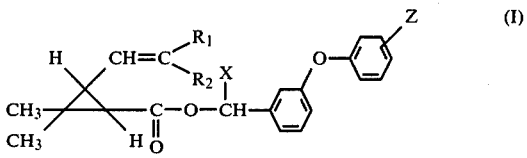

wherein $R_1$ and $R_2$ are independently selected from fluorine, chlorine and bromine; X is hydrogen, cyano or ethynyl; and Z is hydrogen, chlorine, fluorine or bromine.

2. A tag according to claim 1, further characterized in that in the compound of formula I, X is hydrogen or cyano and Z is hydrogen.

3. A tag according to claim 1 or 2, further characterized in that the compound of formula I is: alpha-cyano-3-phenoxybenzyl 2,2-dimethyl-3-(2,2-di-chlorovinyl)-cyclopropane carboxylate.

4. A tag according to claim 1 or 2, further characterized in that the compound of formula I is 3-phenoxybenzyl 2,2-dimethyl-3-(2,2-dichlorovinyl)cyclopropane carboxylate.

5. A tag according to claim 1 or 2, further characterized in that the compound of formula I forms 1 to 20% by weight of the tag.

6. A tag according to claim 1 or 2, further characterized in that the compound of formula I forms 5 to 15% by weight of the tag.

7. A tag according to claim 1 or 2, further characterized in that the compound of formula I forms about 10% by weight of the tag.

8. A tag according to claim 1 or 2, further characterized in that the macromolecular substance is a polymer or copolymer of vinyl chloride.

9. A method of controlling fly and tick populations on or in the vicinity of an animal, characterized by affixing to an ear of the animal an ear tag according to claim 1 or 2.

* * * * *